(12) United States Patent
Hancock et al.

(10) Patent No.: US 11,253,313 B2
(45) Date of Patent: Feb. 22, 2022

(54) ELECTROSURGICAL FORCEPS INSTRUMENT

(71) Applicant: CREO MEDICAL LIMITED, Chepstow (GB)

(72) Inventors: Christopher Hancock, Bath (GB); George Ullrich, Bangor (GB); David Webb, Bangor (GB); Steven Morris, Chepstow (GB); Patrick Burn, Chepstow (GB); Malcolm White, Chepstow (GB); Thomas Craven, Chepstow (GB)

(73) Assignee: CREO MEDICAL LIMITED, Chepstow (GB)

( * ) Notice: Subject to any disclaimer, the term of this patent is extended or adjusted under 35 U.S.C. 154(b) by 633 days.

(21) Appl. No.: 16/074,353

(22) PCT Filed: May 16, 2017

(86) PCT No.: PCT/EP2017/061741
§ 371 (c)(1),
(2) Date: Jul. 31, 2018

(87) PCT Pub. No.: WO2017/198672
PCT Pub. Date: Nov. 23, 2017

(65) Prior Publication Data
US 2019/0167342 A1 Jun. 6, 2019

(30) Foreign Application Priority Data

May 17, 2016 (GB) ..................................... 1608632

(51) Int. Cl.
*A61B 18/14* (2006.01)
*A61B 18/18* (2006.01)
(Continued)

(52) U.S. Cl.
CPC ...... *A61B 18/1447* (2013.01); *A61B 18/1815* (2013.01); *A61B 2017/0034* (2013.01);
(Continued)

(58) Field of Classification Search
CPC .................................................. A61B 18/1815
See application file for complete search history.

(56) References Cited

U.S. PATENT DOCUMENTS 6,585,735 B1 7/2003 Frazier et al.
2010/0179547 A1* 7/2010 Cunningham ..... A61B 18/1445
606/51

(Continued)

FOREIGN PATENT DOCUMENTS

EP 2 233 098 A1 9/2010
EP 2 601 904 A1 6/2013
(Continued)

OTHER PUBLICATIONS

British Search Report dated Oct. 19, 2016 issued in British Application No. GB1608632.4.
(Continued)

*Primary Examiner* — Ronald Hupczey, Jr.
(74) *Attorney, Agent, or Firm* — Arent Fox LLP

(57) ABSTRACT

An electrosurgical forceps instrument in which an energy conveying structure for efficiently transferring electromagnetic energy (e.g. microwave energy and/or radiofrequency energy) from a coaxial cable to electrodes on the forceps jaws is incorporated into a compact jaw opening structure. The jaw opening structure may be dimensioned to be suitable for insertion down the instrument channel of a endoscope or other scoping device. Alternatively, the device may be configured as a laparoscopic device or be used in open procedures. The instrument may be used as a tool to perform new minimally invasive surgical techniques such as (Continued)

Natural Orifice Transluminal Endosurgery (NOTES) or the like.

25 Claims, 6 Drawing Sheets

(51) Int. Cl.
*A61B 18/00* (2006.01)
*A61B 17/00* (2006.01)

(52) U.S. Cl.
CPC .......... *A61B 2018/0063* (2013.01); *A61B 2018/00077* (2013.01); *A61B 2018/00589* (2013.01); *A61B 2018/00595* (2013.01); *A61B 2018/00607* (2013.01); *A61B 2018/00982* (2013.01); *A61B 2018/00994* (2013.01); *A61B 2018/1455* (2013.01); *A61B 2018/1823* (2013.01); *A61B 2018/1861* (2013.01)

(56) References Cited

U.S. PATENT DOCUMENTS

| | | | |
|---|---|---|---|
| 2010/0249769 A1* | 9/2010 | Nau, Jr | A61B 18/1815 606/33 |
| 2012/0150167 A1 | 6/2012 | Fischer et al. | |
| 2013/0023871 A1 | 1/2013 | Collins | |
| 2013/0046303 A1 | 2/2013 | Evans et al. | |
| 2013/0144284 A1* | 6/2013 | Behnke, II | A61B 18/1815 606/33 |
| 2013/0253508 A1 | 9/2013 | Ide | |

FOREIGN PATENT DOCUMENTS

| | | |
|---|---|---|
| GB | 2 487 288 A | 7/2012 |
| WO | WO 2012/076844 A1 | 6/2012 |
| WO | WO 2015/052502 A1 | 4/2015 |
| WO | WO 2015/097472 A1 | 7/2015 |
| WO | WO 2016/059209 A1 | 4/2016 |

OTHER PUBLICATIONS

Carbonell et al., "A comparison of laparoscopic bipolar vessel sealing devices in the hemostasis of small-, medium-, and large-sized arteries" J Laparoendosc Adv Surg Tech 13(6) 377-380; 2003.
International Search Report and Written Opinion dated Jul. 14, 2017 issued in International Application No. PCT/EP2017/061741.
Presthus et al., "Vessel sealing using a pulsed bipolar system and open forceps" J Am Assoc Gynecol Laparosc 10(4): 528-533, 2003.
Richter et al., "Efficacy and quality of Vessel sealing" Surg Endosc (2006)20: 890-894.

* cited by examiner

ELECTROSURGICAL FORCEPS INSTRUMENT

CROSS-REFERENCE TO RELATED APPLICATIONS

This application is a 35 U.S.C. § 371 National Phase of PCT Application No. PCT/EP2017/061741 filed May 16, 2017, which claims priority to British Application No. GB 1608632.4 filed May 17, 2016. The disclosures of these prior applications are hereby incorporated by reference herein.

FIELD OF THE INVENTION

The invention relates to electrosurgical forceps for grasping biological tissue and for delivering microwave energy into the grasped tissue to coagulate or cauterise or seal the tissue. In particular, the forceps may be used to apply pressure to close one or more blood vessels before applying electromagnetic radiation (preferably microwave energy) to seal the blood vessel(s). The forceps may also be arranged to cut tissue after coagulate or sealing, e.g. using radiofrequency (RF) energy or a mechanical cutting element, such as a blade. The invention may be applied to forceps that can be inserted down the instrument channel of an endoscope, a gastroscope or a bronchoscope, or may be used in laparoscopic surgery or open surgery.

BACKGROUND TO THE INVENTION

Forceps capable of delivering heat energy into grasped biological tissue are known [1]. For example, it is known to deliver radiofrequency (RF) energy from a bipolar electrode arrangement in the jaws of the forceps [2,3]. The RF energy may be used to seal vessel by thermal denaturation of extracellular matrix proteins within the vessel wall. The heat energy may also cauterise the grasped tissue and facilitate coagulation.

U.S. Pat. No. 6,585,735 describes an endoscopic bipolar forceps in which the jaws of the forceps are arranged to conduct bipolar energy through the tissue held therebetween.

EP 2 233 098 describes microwave forceps for sealing tissue in which the sealing surfaces of the jaws include one or more microwave antennas for radiating microwave energy into tissue grasped between the jaws of the forceps.

WO 2015/097472 describes electrosurgical forceps in which one or more pairs of non-resonant unbalanced lossy transmission line structure are arranged on the inner surface of a pair of jaws.

SUMMARY OF THE INVENTION

At its most general, the present invention provides an electrosurgical forceps instrument in which an energy conveying structure for efficiently transferring electromagnetic energy (e.g. microwave energy and/or radiofrequency energy) from a coaxial cable to electrodes on the forceps jaws is incorporated into a compact jaw opening structure. The jaw opening structure may be dimensioned to be suitable for insertion down the instrument channel of a endoscope or other scoping device. Alternatively, the device may be configured as a laparoscopic device or be used in open procedures. The instrument may be used as a tool to perform new minimally invasive surgical techniques such as Natural Orifice Transluminal Endosurgery (NOTES) or the like.

The instrument may be used as a vessel sealer, whereby the jaw structure is configured to deliver enough pressure to the walls of a vessel to close the vessel prior to application of microwave energy to walls of the vessel to develop a coagulated plug that can effectively seal the vessel. The instrument may be capable of delivering RF energy to cut tissue. For example, a vessel may be cut by creating two seals using microwave energy and then applying RF energy at a location between the two microwave seals to cut or part the vessel. Such functionality may find use for example in performing lobectomy of the lungs or liver.

The energy conveying structure makes use of a flexible, i.e. deformable, structure for conveying the electromagnetic energy from the coaxial cable to the jaw structure. This enables the jaw structure to move relative to the coaxial cable without affecting delivery of the electromagnetic energy. The flexible structure may comprises a flexible substrate that forms the basis of a transmission line structure, which can be a coaxial structure, a microstrip type transmission line structure, or a shielded stripline. The dimensions of the transmission line structure can be tuned to improve an impedance match between the coaxial cable and the electrodes of the forceps jaws.

According to the invention, there is provided an electrosurgical forceps comprising: a coaxial cable for conveying microwave energy; a pair of jaws mountable at a distal end of the coaxial cable, the pair of jaws being movable relative to each other to open and close a gap between opposing inner surfaces thereof, wherein the pair of jaws comprises a first jaw having: an outer jaw element operably engagable with an actuating element for causing relative movement between the pair of jaws, an inner jaw element attached to the outer jaw element to form the inner surface of the first jaw, the inner jaw element comprising an applicator pad having a first electrode and an second electrode formed thereon, and an energy transfer element for conveying microwave energy from the coaxial cable to the first electrode and second electrode, and wherein the energy transfer element comprise a flexible dielectric substrate having a pair of conductive tracks formed thereon. In use, the pair of jaws may be arranged to grip biological tissue, e.g. a blood vessel, and apply microwave energy across the gap between the inner surface of the jaws to coagulate the tissue contained within the vessel, i.e. collagen, elastin, fat or blood or a combination of in the biological tissue and therefore seal the gripped vessel. After sealing, the vessel may be cut, e.g. using a blade or RF energy delivered from the same electrodes that deliver the microwave energy. A movable blade may thus be incorporated into the forceps.

Although the electrodes may be provided on only one of the jaws, it is desirable for them to be provide on both jaws, so that the coagulating effect of the microwave energy is applied in an even manner, which should create a better seal. Thus, the pair of jaws may comprise a second jaw disposed opposite the first jaw, the second jaw having an identical structure to the first jaw.

The first and second electrodes may be elongate conductive elements formed on the applicator pad. They may be parallel transmission lines, and may form a co-planar line structure on the applicator pad. The distance of separation between the co-planar lines or parallel transmission lines may be chosen to provide RF cutting functionality, i.e. to enable an E-field produced upon applying RF energy to be high enough to produce tissue cutting or dissection/resection. The parallel transmission electrodes may be arranged such that the electrodes that opposed each other across the gap between the jaws are of opposite polarity, i.e. a positive charge on one line faces a negative charge of the opposing line. The tissue cutting action may be augmented by the opposing E-fields on the two opposite faces when the jaws are in close proximity, e.g. equal to or less than 1 mm apart, preferably equal to or less than 0.5 mm apart. The spacing between the first and second electrodes on the jaw may be equal to or less than 0.5 mm.

RF energy may be applied between the first and second electrodes and/or may be applied in a similar manner to that of conventional RF bipolar sealers, where one jaw is at one polarity and the facing jaw is at the opposite polarity. In this case, it is preferable for the connections to opposing jaws to be swapped over so that when the jaws are in close proximity to each other the polarity of the two sets of electrodes that face one another, i.e. like poles attract.

The invention may comprise one of or more of the following features, in any combination.

The pair of conductive tracks may be formed on opposite sides of the flexible dielectric substrate. For example, the pair of conductive tracks may comprise a first conductive track electrically connected to an inner conductor of the coaxial cable, and a second conductive track electrically connected to an outer conductor of the coaxial cable.

The first conductive track may be electrically connected to the first electrode and the second conductive track is electrically connected to the second electrode. These connections may occur at a junction on the applicator pad. The conductive tracks may connect to opposite sides of the applicator pad. The applicator pad may have a hole formed therethrough, whereby one of the first electrode and second electrode is connected to one of the pair of conductive tracks via the hole.

The outer jaw element may be formed from a rigid material to give structural strength to the pair of jaws. For example, the outer jaw element may be formed from stainless steel or nitinol. The outer jaw element may be preformed (e.g. by heat treatment) in a shape that holds the inner surfaces of the jaws away from each other. Thus, the jaws may naturally occupy an open configuration.

In order to deform in a predictable or repeatable manner, the outer jaw element may be articulated. For example, the outer jaw element may comprise one or more living hinges, e.g. formed by regions of reduced material thickness on the outer jaw element. The outer jaw elements may be articulated to provide a pantograph-type structure where the gap between applicator pads is uniform along the length of the jaws as they are opened and closed. This structure can prevent tissue from getting pushed out of the jaws as they are closed.

The flexible dielectric substrate may be a ribbon having a width greater than a width of the pair of conductive tracks. The applicator pad may comprise an additional piece of dielectric (e.g. ceramic or PTFE or ceramic loaded PTFE) mounted on the inner jaw element. Alternatively, the applicator pad may be an exposed distal portion of the flexible substrate. In order to minimise power loss in the flexible substrate that connects the coaxial feed cable to the energy delivery applicators and to ensure the material can withstand voltages associated with RF cutting, i.e. peak voltages of up to 400 V or more, the material preferably has a low dissipation factor or tan delta, i.e. 0.001 or lower, and has a high dielectric strength or breakdown voltage, i.e. up to 100 kV/mm or more. Polyimide or similar materials can be used.

The first electrode and second electrode may comprise parallel elongate strips of conductive material on the inner surface of the jaw.

The energy transfer element may be dimensioned to match an impedance of the coaxial cable with an impedance of the first electrode and second electrode and the biological tissue that makes contact with the electrode.

The actuating element may be a sleeve slidably mounted on the coaxial cable. In use, the sleeve may slide over the back surfaces of the outer jaw elements to force them towards one another to close the pair of jaws. The sleeve may comprise two portions. A first (proximal) portion may comprise a long (e.g. equal to or greater than 1 m) flexible section that can be articulated or moved within the instrument channel and yet provide a level of rigidity without deforming or bending. The first portion may be made from PEEK or the like. A second (distal) portion may comprise a short section e.g. equal to or less than 10 mm, of more rigid material, e.g. a metal or hard plastic, that can be pushed over the jaws and apply enough force to close the jaws.

The pair of jaws may be dimensioned to fit within an instrument channel of a surgical scoping device. For example, the maximum outer diameter of the pair of jaws (and sleeve) may be equal to or less than 2 mm.

In another aspect, the invention provides an electrosurgical apparatus comprising: an electrosurgical generator for supplying microwave energy; a surgical scoping device (e.g. endoscope or similar) having an instrument cord for insertion into a patient's body, the instrument cord having an instrument channel extending therethrough; an electrosurgical forceps as set out above mounted in the instrument channel; and a handle for actuating the forceps, wherein the coaxial cable is connected at its proximal end to receive microwave energy from the electrosurgical generator, and wherein the actuating element is operably connected to the handle. As discussed above, the forceps may be arranged also to deliver RF energy, e.g. for the purposes of cutting the tissue. The RF energy may come from the same generator as the microwave energy.

The actuating element may be a sleeve that extends around and is axially slidably relative to the coaxial cable. The handle may comprise an actuation mechanism for controlling axial movement of the sleeve, the actuation mechanism comprising: a body fixed in the handle; a carriage slidable relative to the body, and a lever pivotably mounted on the body and operably engaged with the carriage, whereby rotation of the lever caused sliding motion of the carriage, wherein the sleeve is attached to the carriage. The actuation mechanism may include a biasing element (e.g. spring) arranged to urge the carriage in a proximal direction, i.e. to urge the sleeve away from the jaws so that the forceps normally occupy an open position.

The first electrode and second electrode may be parallel elongate conductive elements arranged to act as both (i) an active electrode and a return electrode for RF energy conveyed by the coaxial cable, and (ii) a lossy transmission line structure for microwave energy conveyed by the coaxial cable. Herein, the term "lossy transmission line structure" may mean a non-uniform unbalanced lossy transmission line for supporting the microwave energy as a travelling wave, the non-uniform unbalanced lossy transmission line being non-resonant for the microwave energy along the travelling wave. The elongate conductive elements may have a proximal end in electrical connection with an inner conductor or an outer conductor of the coaxial cable and an open circuit distal end. This arrangement places fewer restrictions on the electrode configuration than in microwave forceps where the electrode must form a radiating antenna. Other configurations of parallel lines are possible, i.e. a two meandering lines, two parallel curved lines, two 'L' shaped lines, etc. The shape of electrodes may be selected based on the desired tissue effect to be achieved.

Herein the term "non-resonant" may mean that the electrical length of the transmission line (along the microwave energy travelling wave) is set to inhibit multiple reflections of the travelling wave, i.e. to prevent or inhibit the creation of a radiating standing wave. In practice this may mean that the electrical length of the transmission line is substantially different from a multiple of a quarter wavelength of the microwave energy (an odd or even multiple needs to be avoided depending on whether the distal end of the transmission line is an open circuit or a short circuit). It is particularly desirable for the transmission line to be non-resonant when there is biological tissue in the gap, i.e. in contact with the jaw elements. Thus, the electrical length of the transmission line may be set to avoid a multiple of a quarter wavelength of the microwave energy when the transmission line is loaded by the biological tissue in this way. Preferably the distal end of the transmission line is an open circuit, as this may enable the device to operate with radiofrequency (RF) energy as well as microwave energy.

Forming a non-resonant transmission line may prevent the device from radiating. The microwave energy is therefore delivered into tissue through leakage from the transmission line structure. By setting the length of the transmission line with knowledge of the loss level into biological tissue at the frequency of the microwave energy, the electrosurgical forceps of the invention can be arranged to deliver substantially all of the power received at the proximal end of the transmission line in a single transit of the travelling wave along the transmission line, thus create optimal tissue coagulation in the shortest possible period of time.

In other words, the geometry of the transmission line is selected, e.g. on the basis of simulations or the like, such that it exhibits high loss in biological tissue at the frequency of the microwave energy. Similarly, the geometry of the transmission line may ensure that much less power is lost when there is no tissue in the gap, but air instead. For example, the device may exhibit about 1 dB return loss, i.e. 80% of power reflected back to the generator, compared to 20% when there is tissue there. Thus, four times as much power can be delivered when tissue is present in the gap. Biological tissue is lossy, i.e. it is a good absorber of microwave energy.

The electrodes may each have a conductive ridge formed thereon. This provides a conductive line that acts as a preferential location for a current path termination. The ridge may be integrally formed with the elongate conductive element, or it may be formed by attaching (e.g. soldering) a rod onto each electrode. The raised ridges thus create poles for the electric field that performs the cutting function when RF energy is supplied. The height of each ridge may be equal to or less than 0.5 mm. A dielectric film may be applied between ridges on the same applicator pad. This can assist in form a preferential path between the top surface of the ridges, and assist in preventing breakdown.

Herein, radiofrequency (RF) may mean a stable fixed frequency in the range 10 kHz to 300 MHz and the microwave energy may have a stable fixed frequency in the range 300 MHz to 100 GHz. The RF energy should have a frequency high enough to prevent the energy from causing nerve stimulation and low enough to prevent the energy from causing tissue blanching or unnecessary thermal margin or damage to the tissue structure. Preferred spot frequencies for the RF energy include any one or more of: 100 kHz, 250 kHz, 400 kHz, 500 kHz, 1 MHz, 5 MHz. Preferred spot frequencies for the microwave energy include 915 MHz, 2.45 GHz, 5.8 GHz, 14.5 GHz, 24 GHz.

As mentioned above, the electrosurgical forceps of the invention may be configured for insertion down an instrument channel of an endoscope for insertion into the upper and lower gastrointestinal tract, or may be arranged for use in laparoscopic surgery or in a NOTES procedure or in a general open procedure.

The invention can be used to seal blood vessels with a wall diameter of less than 2 mm to over 7 mm.

The invention may also be expressed as an electrosurgical device that can be used to deliver microwave energy to create plugs to seal vessels and can use RF energy delivered using electric fields set up between planar parallel microstrip lines and/or lines on opposing jaws that are of opposite polarity to cut or part the vessel.

The invention may also be expressed as an electrosurgical device that can be used to deliver microwave energy to create plugs to seal vessels and that has a mechanical blade to part or cut the vessel.

The invention may be used in a vessel sealing procedure whereby two seals or plugs are made using the microwave energy and then the vessel is parted (e.g. at the centre point between the two plugs) using either RF energy or a mechanical blade. In the latter case, the blade may be arranged to be located between the two radiating jaws and use a separate actuator to deploy the mechanical blade at the end of the sealing procedure, when it is required to part the vessel.

BRIEF DESCRIPTION OF THE DRAWINGS

Embodiments of the invention are described in detail below with reference to the accompanying drawings, in which.

DETAILED DESCRIPTION; FURTHER OPTIONS AND PREFERENCES

Figure 1:
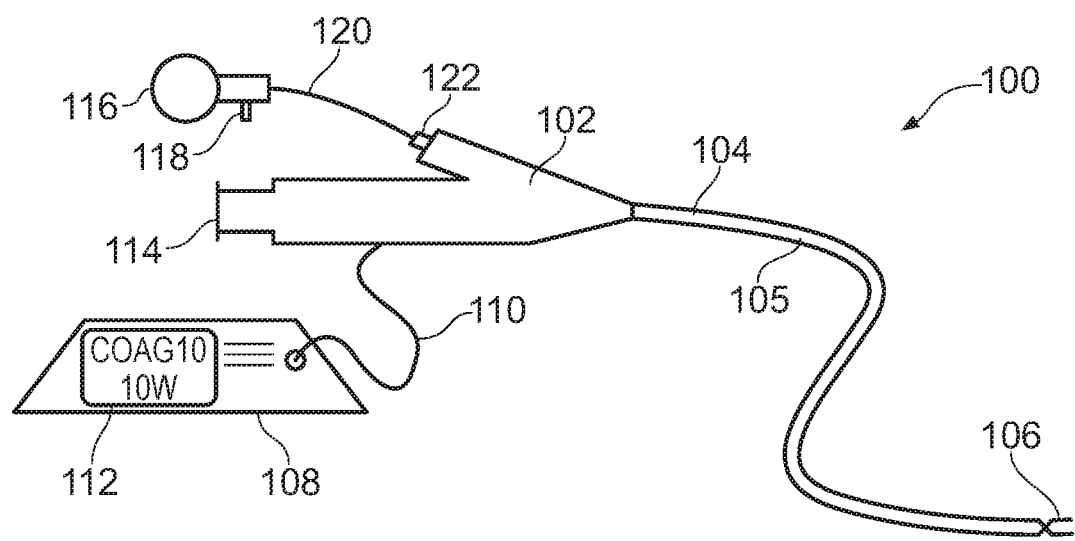
FIG. 1 is a schematic diagram showing an electrosurgery apparatus in which the present application can be used.

The present invention relates to an electrosurgical forceps device capable of delivering microwave energy to seal blood vessels. The device may be used in open surgery, but may find particular use in procedures where there is restricted access to the treatment site. For example, the electrosurgical forceps of the invention may be adapted to fit within the instrument channel of a surgical scoping device i.e. laparoscope, endoscope, or the like. FIG. 1 shows a schematic view of an electrosurgery apparatus 100 in which the electrosurgical forceps of the invention may be used.

The electrosurgery apparatus 100 comprises a surgical scoping device 102, such as an endoscope or laparoscope. The surgical scoping device 102 has an instrument cord 103 suitable for insertion into a patient's body. Running within the instrument cord is an instrument channel 105, which provides access for surgical instruments to the distal end of the instrument cord 104. In this example, a distal tip assembly of a forceps instrument 106 can be seen protruding from the distal tip from the instrument channel 105.

The electrosurgery apparatus may comprise an electrosurgical generator 108 capable of generating and controlling power to be delivered to the instrument 106, e.g. via power cable 110, which extends from the generator 108 through the scoping device 102 and instrument channel 105 to the distal tip. Such electrosurgical generators are known, e.g. as disclosed in WO 2012/076844. The electrosurgical generator 108 may have a user interface (not shown) for selecting and/or controlling the power delivered to the instrument 106. The generator 108 may have a display 112 for showing the selected energy delivery mode.

The surgical scoping device 102 may be conventional. For example, it may comprise an eyepiece 114 or other optical system for providing an image of the distal tip. Operation of the instrument 106 may be done via a control wire 102 or sleeve 112 that extends through the instrument channel 105. An operator may control movement of the control wire 120 or sleeve 122 via a handle 116 which comprises an actuator 118, which may be a slidable trigger or rotatable dial or lever.

Embodiments of the present invention represent a development of the electrosurgical forceps disclosed in WO 2015/097472, and in particular relate to the structure of the distal tip assembly, which provides control over the opening and closing of the forceps whilst also delivering the necessary power to achieve vessel sealing by coagulation.

Figure 2:
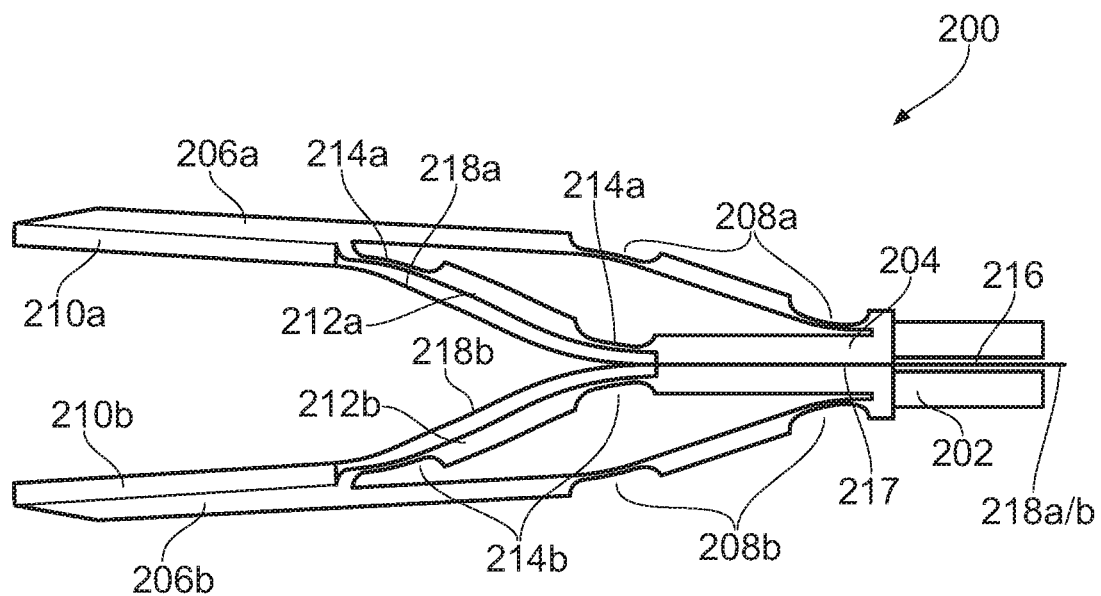
FIG. 2 is a schematic cross sectional view through a distal tip assembly for electrosurgical forceps that is an embodiment of the invention.

FIG. 2 shows a cross sectional view through a distal tip assembly 200 for an electrosurgical forceps device that is an embodiment of the invention. The distal tip assembly 200 comprises proximal support sleeve 202 that acts as a structural base for a pair of movable jaw elements 206a, 206b. The proximal support sleeve 202 may be secured (e.g. via a suitable rigid frame or connector) to a coaxial cable (not shown) that delivers power to the forceps. A jaw base 204 is mounted on or integrally formed with the proximal support sleeve 202 at its distal end. In this embodiment, the jaw base 204 has a pair of opposed jaw elements extending therefrom in a distal direction. Each jaw comprises an outer jaw element 206a, 206b and an inner jaw element 202a, 202b. The jaws may be formed from a rigid, inert material, such as stainless steel or the like. Each of the outer jaw elements 206a, 206b comprises a pair of living hinges 208a, 208b integrally formed therein, towards a proximal end of the jaw. Similarly, each of the inner jaw elements 212a, 212b have a pair of living hinges 214a, 214b. The living hinges are arranged to enable the inner and outer jaw elements to articulate in a manner whereby the inner opposing surfaces of the jaws can move towards each other and away from each other, to open and close the jaws. Movement of the jaw elements may be controlled by one or more axially moveable control wires (not shown) which can extend through the instrument channel and be controlled by an operator.

In order to deliver microwave power to biological tissue that is grasped between the inner opposing surfaces of the jaws, each outer jaw element 206a, 206b has a dielectric applicator pad 210a, 210b attached to its inner surface. The applicator pads 210a, 210b may be formed from ceramic, for example. A pair of electrodes (not shown) may be formed on the exposed opposing surfaces of the applicator pads 210a, 210b in order to deliver microwave energy. The electrodes may be configured in a way similar to that disclosed in WO 2015/097472, although other configurations are possible. However, it is desirable that the pair of electrodes on each applicator pad 210a, 210b are in electrical communication respectively with an inner and outer conductor of a coaxial cable (not shown) which supplies power to the distal tip assembly 200.

In order to convey power from the coaxial cable to the applicator pads 210a, 210b, the distal tip assembly 200 comprises a pair of flexible substrates 218a, 218b which extend from a proximal portion of the applicator pads 210a, 210b through a channel 217 formed in the jaw base 204 and a channel 216 formed in the proximal support sleeve 202 to a distal end of the coaxial cable which is located proximally to the proximal support sleeve 202.

Each flexible substrate 218a, 218b may be in the form of a ribbon of dielectric material, such as the Rflex microwave substrate manufactured by Rogers Corporation. Each of the flexible substrates 218a, 218b may have a pair of conductive strips formed thereon, which serve to electrically connect the electrodes formed on the applicator pads 210a, 210b respectively with the inner and outer conductor of the coaxial cable. The conductive strips may be layers of metallisation formed opposite surfaces of the flexible substrates 218a, 218b. The dimensions of the dielectric ribbon (e.g. its width and length) and the metallisation tracks may be selected to enable a good match to be achieved between the coaxial cable and the electrodes on the applicator pads 210a, 210b.

Figure 3A:
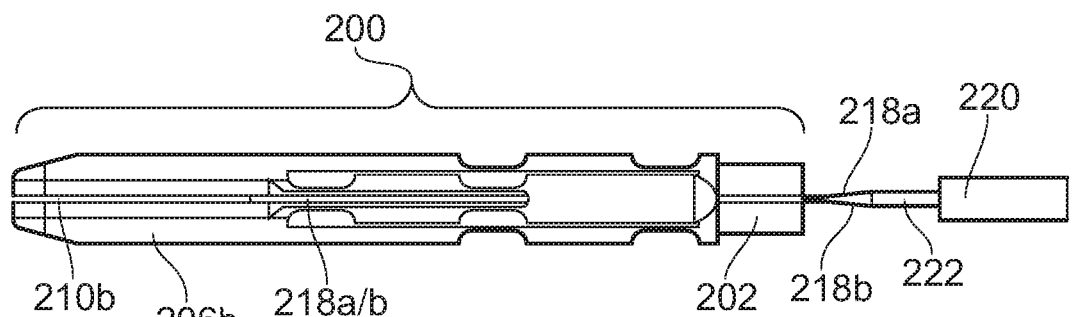
FIG. 3A is a cross sectional view through a distal portion of the electrosurgical forceps shown in FIG. 2 in a closed position.

FIG. 3A shows a side view of the distal tip assembly 200 in a closed configuration, where the opposed surfaces of applicator pads 210a, 210b are brought together. In this view, it can be seen that the flexible substrates 218a, 218b extend distally from the proximal support sleeve 202. The substrates separate at this point and engage (and electrically connect to) a protruding section of inner conductor 222, which in turn extends in a distal direction from the rest of coaxial cable 220. An example of how this connection can be achieved is discussed in more detail below.

Figure 3B:
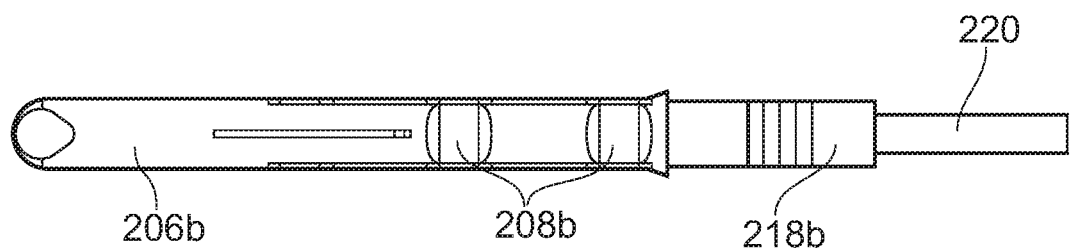
FIG. 3B is a bottom view of the electrosurgical forceps shown in FIG. 3A.

FIG. 3B shows a bottom view of the forceps instrument shown in FIG. 3A. Here it can be seen that the ribbon of flexible dielectric can have a width similar to that of the jaws.

Figure 4A:
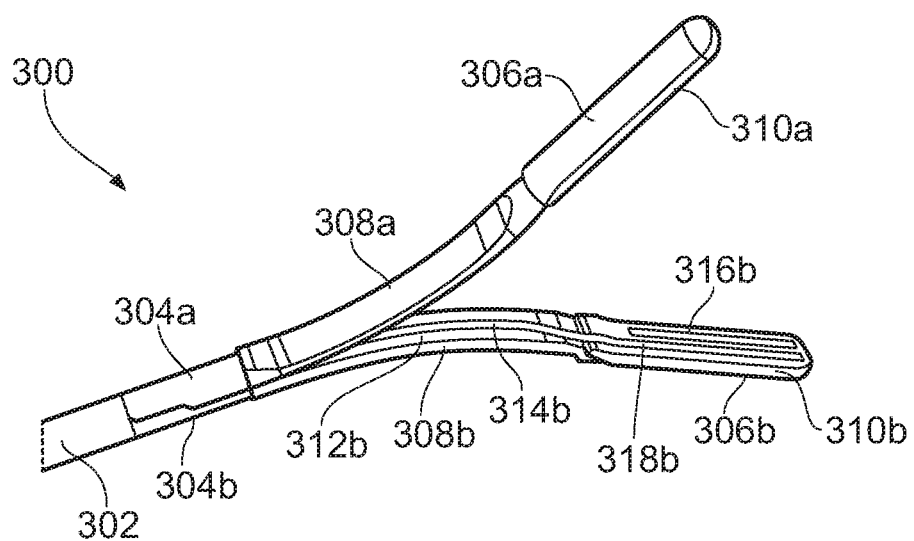
FIG. 4A is a schematic perspective view of a distal tip assembly for an electrosurgical forceps that is another embodiment of the invention.

FIG. 4A shows a perspective view of a distal tip assembly 300 for an electrosurgical forceps device that is another embodiment of the invention. This embodiment presents a structurally simpler jaw structure, in which the outer jaw element is formed from a single piece of material (e.g. Nitinol or stainless steel) which is heat formed before assembly so that the jaws are biased towards the open position shown in FIG. 4A.

The distal tip assembly 300 shown in FIG. 4A comprises a pair of separate jaw elements which are mounted together at their respective proximal jaw bases 304a, 304b to the distal end of a coaxial cable 302. Each jaw element comprises three sections: the jaw base 304a, 304b which attaches to the coaxial cable 302, an intermediate flexible portion 308a, 308b; and a distal electrode support 306a, 306b. A ceramic pad 310a, 310b is affixed to the opposing inner surfaces of the distal portions 306a, 306b of each jaw element in a manner similar to that discussed above.

In this embodiment, a flexible substrate 312a, 312b is attached (e.g. adhered) to the inner surfaces of each jaw element. The flexible substrate may extend beneath its respective applicator pad. Similarly to the embodiment discussed above, each flexible substrate have a pair of conductive elements formed thereon, e.g. on opposite sides thereof. In FIG. 4A, the flexible substrate 312b of the lower jaw element can be seen, on which a conductive element 314b extends to connect to an electrode 318b formed on the applicator 310b. A second electrode 316b is formed next to the electrode 318b on the applicator pad 310b. The electrodes 316b, 318b together form a parallel line structure for delivering microwave and radiofrequency (RF) energy. The electrode 316b is attached to a second conductive element (not shown in FIG. 4A) on the flexible substrate 312b in a manner that is described below.

The dimensions of the applicator pad and electrodes shown in FIG. 4A may be selected to enable microwave power to be delivered efficiently. For example, the length of the applicator pad 310b (which may be made of ceramic) can be 10 mm. Its width may be equal to or less than 2 mm. A gap between the electrodes 316b, 318b may be equal to or less than 0.4 mm. The width of the flexible substrate 312b may be less than the width of its respective applicator, e.g. equal to or less than 1.8 mm. The length of the flexible substrate 312b between the coaxial cable and the applicator pad may be 22 mm. As described above, the flexible substrate may be formed from any suitable dielectric material, e.g. the Rflex® manufactured by Rogers Corporation, or Ultralam® dielectric laminate material, e.g. formed from liquid crystalline polymer, also manufactured by Rogers Corporation.

Figure 4B:
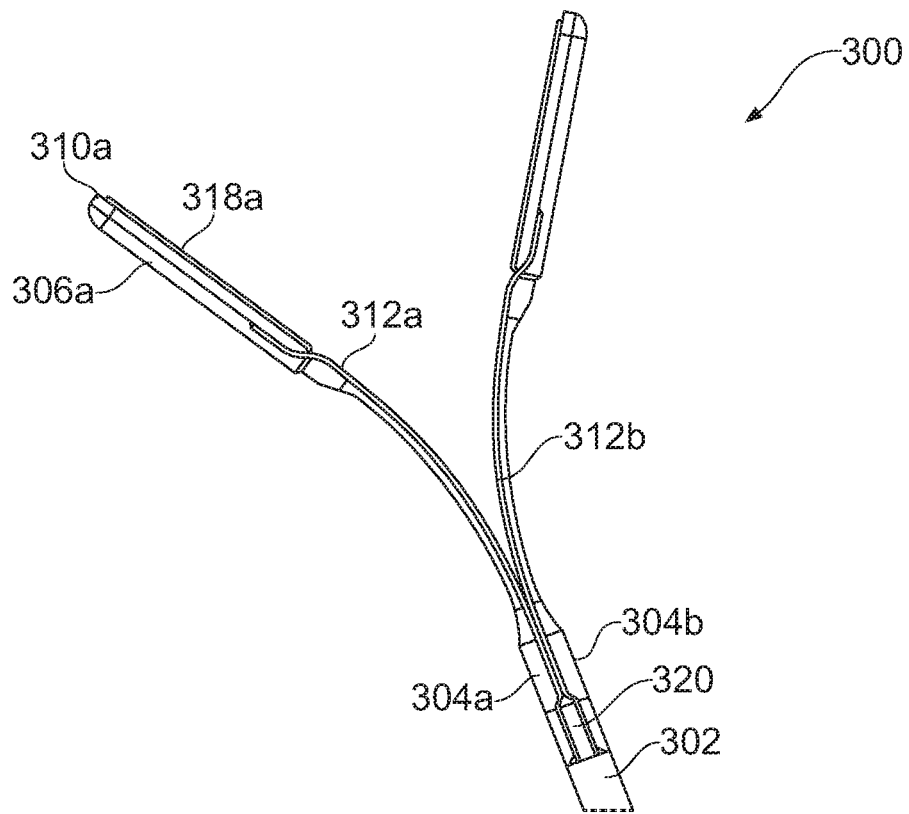
FIG. 4B is a side view of the electrosurgical forceps shown in FIG. 4A.

FIG. 4B shows a side view of the dielectric tip assembly 300 in its natural open configuration. Here it can be seen that an inner conductor 320 of the coaxial cable 302 protrudes from a distal end thereof, where it is electrically connected the conductive element on the inner surface of the flexible substrates 312a, 312b. In use, the forceps jaws in this embodiment may be closed by sliding an outer sleeve (not shown) along the device to bring the jaws together. This mode of functionality is discussed below with respect to FIGS. 5A to 5C.

Figure 4C:
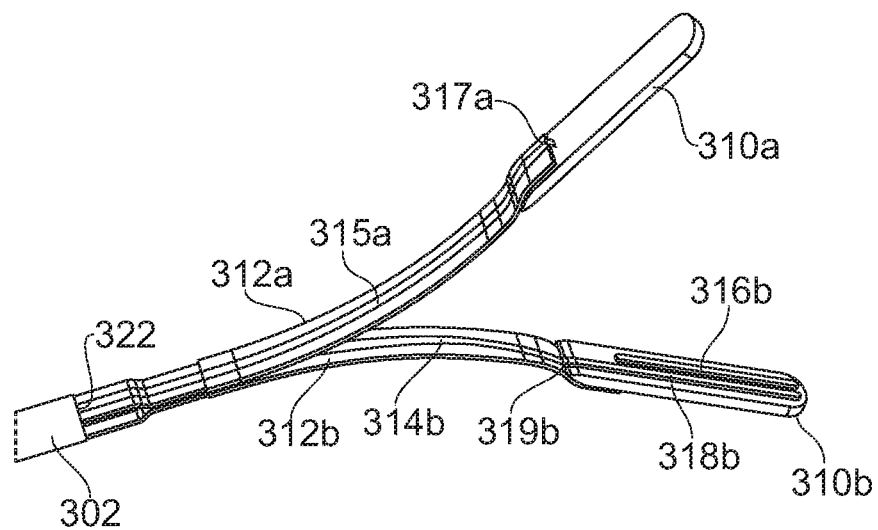
FIG. 4C is a perspective view of the electrosurgical forceps shown in FIG. 4A with the jaw structure removed.

FIG. 4C shows a view of the distal end assembly shown in FIG. 4A without the jaw elements. Here it can be seen that the flexible substrates 312a, 312b extend from an interface 322 at the distal end of the coaxial cable 302 to a proximal region on each of the applicator pads 310a, 310b. As shown in FIG. 4C, the upper flexible substrate 312a has a first conductive element 315a on an upper surface thereof, which is connected at its proximal end to an outer conductor of the coaxial cable 302. This conductive element connects to an electrode on the inner exposed surface of the applicator pad 310a via a through hole 317a in the applicator pad, which is filled with electrically conductive material. The flexible substrate 312a has another conductive track (not visible in FIG. 4C) on this opposite surface which provides an electrical connection from the inner conductor of the coaxial cable 302 to another electrode on the applicator pad 310a.

The lower flexible substrate shown in FIG. 4C is configured in an identical manner to the upper flexible substrate 312a. Thus it can be seen that the lower flexible substrate 312b has an inner conductive element 314b on its inner surface, which connects to an electrode 318b on the applicator pad 310b at a junction 319b. A second electrode 316b on the applicator pad 310b connects to an outer conductive element (not visible in FIG. 4C) via a through hole in the applicator pad 310b as described above.

Figure 5A:
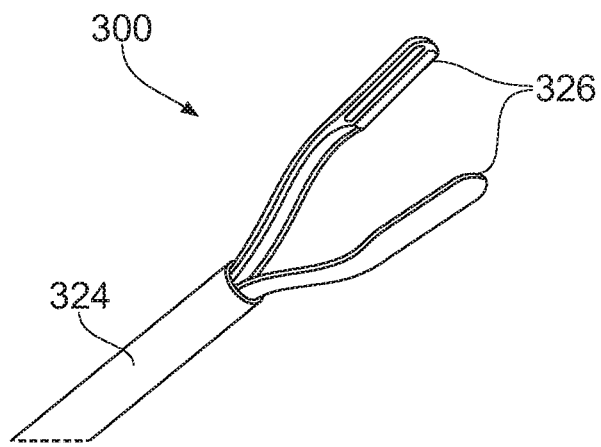
FIGS. 5A, 5B and 5C are perspective views showing the closure operation of an electrosurgical forceps that is an embodiment of the invention.
Figure 5B:
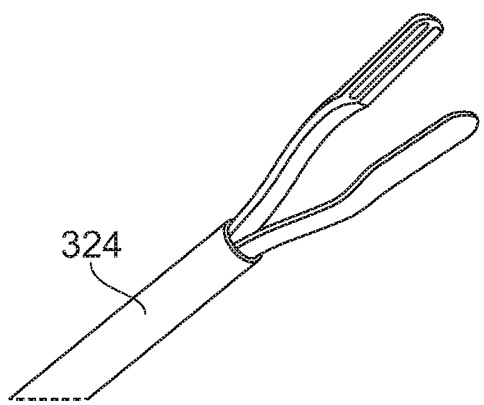
Figure 5C:
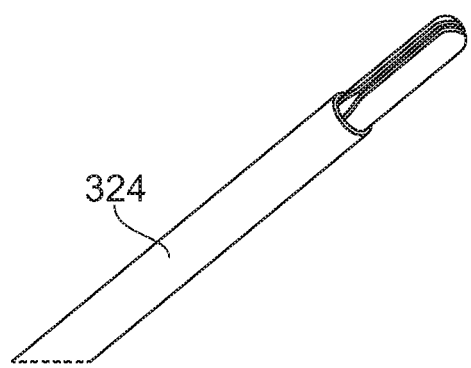

FIGS. 5A, 5B and 5C show different stages in a closing operation for a distal tip assembly 300 as described above. In these drawings, a sleeve 324 is movable axially relative to the jaws 326. As it moves in a distal direction, the sleeve forces the jaw elements to move towards each other as it engages the intermediate portion thereof. FIG. 5C shows the forceps device in a closed configuration in which the applicator pads are brought together. The sleeve may be made from any material having a suitable strength to cause the jaw elements to move together. It may, for example be made from PEEK. Since the movable sleeve 324 needs to slide with respect to the coaxial cable, the coaxial cable may have a lubricious coating formed thereon.

In use, the forceps device of the invention can be inserted down the instrument channel of a surgical scoping device, or used in any other procedure, e.g. in open surgery or with a laparoscope. The device begins in an open configuration as shown in FIG. 5A, where it can be manipulated to position biological tissue (e.g. the stem of a polyp or the like) in between the jaws. Once in position, the jaws can be physically closed by moving the sleeve in order to grasp the tissue and make good contact between the electrodes and the tissue. Microwave energy can be supplied through the coaxial cable to the electrodes, where it is delivered into the tissue to coagulate the blood vessel or vessels that are grasped. The forceps is capable of applying pressure to the blood vessels at the same time as supplying the energy in order to create a good seal. After the vessel is sealed, it may be cut, e.g. by delivering radiofrequency (RF) energy to the electrodes, or by having a mechanical cutting element (e.g. a blade or the like) mounted within the device that can be deployed.

Figure 6:
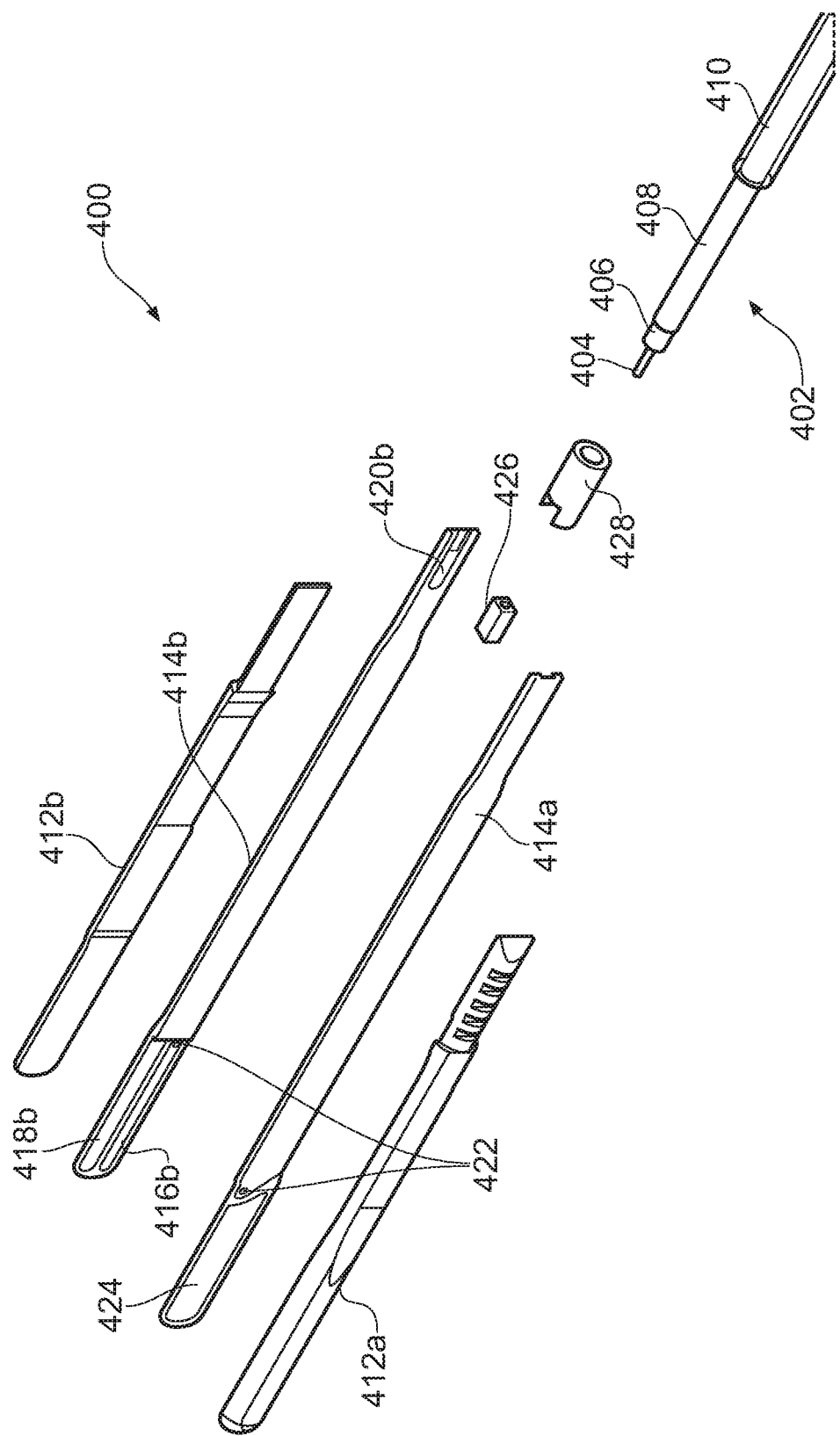
FIG. 6 is an exploded view of a jaw structure for an electrosurgical forceps that is an embodiment of the invention.

FIG. 6 shows an exploded view of a distal tip assembly 400 of an electrosurgical forceps device that is another embodiment of the invention. The distal tip assembly 400 functions in a similar manner to that shown in FIGS. 4A, 4B and 4C in that it comprises an pair of jaw elements that are heat-formed or otherwise pre-treated so that they naturally rest in the open configuration. To close the jaws, an axially slidable sleeve (not shown) is moved over the jaw elements to force them towards each other.

Similarly to the embodiments discussed above, the distal tip assembly is affixed to the distal end of a coaxial cable 402. In this embodiment, the coaxial cable 402 comprises an inner conductor 404 separated from an outer conductor 408 by a dielectric material 406. This structure is enclosed in an outer jacket 410 that may be made of PTFE or similar over which the actuation sleeve (not shown) slides.

Portions of the inner conductor 404 and outer conductor 408 are exposed at the distal end of the coaxial cable 402 in order to electrically connect to electrodes formed on the jaw elements, as described below.

In this embodiment, each jaw comprises an outer jaw element 412a, 412b formed from stainless steel or nitinol that is pre-formed into the open configuration as discussed above. Attached to the inner surface of each outer jaw element 412a, 412b is an inner jaw element 414a, 414b, which in this embodiment is a multi-layer laminate structure. The laminate structure comprises a layer of flexible substrate having a grounded layer of conductive material (e.g. gold or the like) on one side, and a conductive track formed on the other side. The conductive track is covered by a second layer of flexible substrate along its length except for a distal length that forms an active electrode 418b and a proximal length 420b that is electrically connected to the inner conductor 404 via a first conductive adaptor 426. The second layer of flexible substrate may be adhered or otherwise affixed to its respective inner jaw element.

A return electrode 416b of electrically conductive material is formed adjacent to the active electrode 418b and is in electrical communication with the grounded layer of conductive material via a hole 422 through the flexible substrate. The grounded layers of conductive material on the inner jaw elements are electrically connected to the outer conductor via a second conductive adaptor 428. The outer jaw elements 412a, 412b may be soldered to their respective inner jaw element. An attachment pad 424 of a suitable metal may be formed on the back surface of each inner jaw element 414a, 414b to ensure a secure solder join.

The first conductive adaptor 426 may be located distally from the second conductive adaptor 428. The first conductive adaptor 426 may have a bore for receiving the inner conductor 404 in a manner that electrically connects these elements to each other. The conductive tracks that form the active electrodes may be in contact with opposite sides of the first conductive adaptor 426.

The second conductive adaptor 428 may be a tube that fits over and electrically connects to the outer conductor 408. The tube may have two distal fingers that project to overlie and electrically connect with the grounded layer of conductive material on each respective inner jaw element 414a, 414b. The junction containing the first conductive adaptor 426 and second conductive adaptor 428 may be potted in a suitable material (e.g. UV cured adhesive) to provide electrical insulation. In one embodiment, the junction may be contained in a tubular housing that anchors the pair of jaw elements to the coaxial cable.

Figure 7:
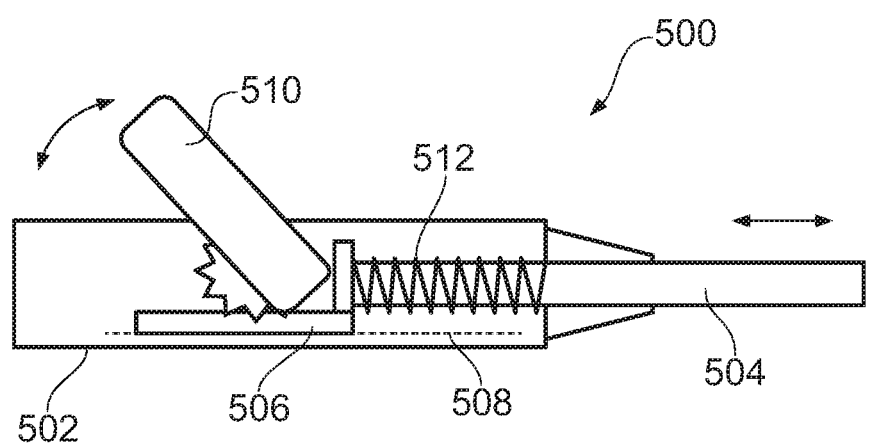
FIG. 7 is a schematic cross-sectional view through an actuator for a sliding sleeve suitable for use with an electrosurgical forceps in an embodiment.

FIG. 7 shows a schematic cross-sectional view of an actuator mechanism 500 for moving a slidable sleeve to operate the electrosurgical forceps described in some embodiments above. The actuator mechanism 500 may be part of the handle 116 discussed with reference to FIG. 1 above. The actuator mechanism 500 comprises a body 502, which may be integrally formed with the handle, having an aperture at a front end thereof from which a flexible sleeve 504 extends. The sleeve 504 is arranged to receive the coaxial cable (e.g. via a side inlet further along its length) and extends together with the coaxial cable to the distal end assembly. The actuator mechanism is arranged to slide the sleeve 504 relative to the coaxial cable to actuate the forceps (i.e. open and close the jaws). A proximal end of the coaxial cable may enclosed in a rigid guide tube within the housing of the actuation mechanism to ensure that it does not bend within the housing.

A proximal end of the sleeve 504 is mounted (e.g. adhered or otherwise secured) on a carriage 506 which slide on a track 508 formed in the body 502. A rotatable lever 510 is pivotably mounted on the body. The lever is operably engaged with the carriage 506 via a rack and pinion type arrangement, whereby rotating the lever 510 relative to the body 502 drives linear motion of the carriage 506 relative to the body, which in turn drives motion of the sleeve 504. A spring 512 is mounted in the body in a manner that acts to bias the carriage to a retracted position (which corresponds to open forceps). The slidable sleeve 504 may be mounted within a outer protective tube (not shown) that is fixed to the body 502.

REFERENCES

[1] Presthus, et al.: Vessel sealing using a pulsed bipolar system and open forceps, *J Am Assoc Gynecol Laparosc* 10(4):528-533, 2003.

[2] Carbonell, et al.: A comparison of laparoscopic bipolar vessel sealing devices in the hemostasis of small-, medium-, and large-sized arteries, J Laparoendosc Adv Surg Tech 13(6):377-380, 2003

[3] Richter, et al.: Efficacy and quality of vessel sealing, *Surg Endosc* (2006) 20: 890-894

The invention claimed is:

1. An electrosurgical forceps comprising:
    a coaxial cable for conveying microwave energy;
    a pair of jaws mountable at a distal end of the coaxial cable, the pair of jaws being movable relative to each other to open and close a gap between opposing inner surfaces thereof,
    wherein the pair of jaws comprises a first jaw having:
        an outer jaw element operably engagable with an actuating element for causing relative movement between the pair of jaws,
        an inner jaw element attached to the outer jaw element to form the inner surface of the first jaw, the inner jaw element comprising an applicator pad having a first electrode and a second electrode formed thereon, and
        an energy transfer element comprising a flexible dielectric substrate which extends from a distal end of the coaxial cable to a proximal portion of the applicator pad, the flexible dielectric substrate having a pair of conductive tracks formed thereon for conveying microwave energy from the coaxial cable to the first electrode and second electrode, wherein the flexible dielectric substrate is flexible to permit flexing of the pair of conductive tracks.

2. An electrosurgical forceps according to claim 1, wherein the pair of jaws comprises a second jaw disposed opposite the first jaw, the second jaw having:
    an outer jaw element operably engagable with an actuating element for causing relative movement between the pair of jaws,
    an inner jaw element attached to the outer jaw element to form the inner surface of the first jaw, the inner jaw element comprising an applicator pad having a first electrode and a second electrode formed thereon, and
    an energy transfer element comprising a flexible dielectric substrate having a pair of conductive tracks formed thereon for conveying microwave energy from the coaxial cable to the first electrode and second electrode.

3. An electrosurgical forceps according to claim 2, wherein the first electrode and second electrode on the first jaw oppose the first electrode and second electrode on the second jaw across the gap between the pair of jaws, and wherein the electrodes that oppose each other across the gap have opposite electrical polarities.

4. An electrosurgical forceps according to claim 3, wherein the coaxial cable is arranged to convey radiofrequency (RF) energy to set up an electric field across the gap that is suitable for cutting biological tissue.

5. An electrosurgical forceps according to claim 1, wherein the pair of conductive tracks are formed on opposite sides of the flexible dielectric substrate.

6. An electrosurgical forceps according to claim 1, wherein the pair of conductive tracks comprise a first conductive track electrically connected to an inner conductor of the coaxial cable, and a second conductive track electrically connected to an outer conductor of the coaxial cable.

7. An electrosurgical forceps according to claim 6, wherein the first conductive track is electrically connected to the first electrode and the second conductive track is electrically connected to the second electrode.

8. An electrosurgical forceps according to claim 1, wherein the applicator pad has a hole formed therethrough, and wherein one of the first electrode and second electrode is connected to one of the pair of conductive tracks via the hole.

9. An electrosurgical forceps according to claim 1, wherein the outer jaw element is preformed to bias the pair of jaws into an open configuration.

10. An electrosurgical forceps according to claim 1, wherein the outer jaw element comprises a living hinge.

11. An electrosurgical forceps according to claim 1, wherein the flexible dielectric substrate is a ribbon having a width greater than a width of the pair of conductive tracks.

12. An electrosurgical forceps according to claim 1, wherein the applicator pad is a piece of ceramic, PEEK or PTFE.

13. An electrosurgical forceps according to claim 1, wherein the applicator pad is an exposed distal portion of the flexible substrate.

14. An electrosurgical forceps according to claim 1, wherein the first electrode and second electrode comprise parallel elongate strips of conductive material on the inner surface of the jaw.

15. An electrosurgical forceps according to claim 14, wherein the parallel elongate strips of conductive material are straight, meandering, 'L' shape, or triangular.

16. An electrosurgical forceps according to claim 1, wherein the energy transfer element is dimensioned to match an impedance of the coaxial cable with an impedance of the first electrode and second electrode.

17. An electrosurgical forceps according to claim 1, wherein the actuating element is a sleeve slidably mounted on the coaxial cable.

18. An electrosurgical forceps according to claim 17, wherein the sleeve comprises a flexible proximal portion and a rigid distal portion.

19. An electrosurgical forceps according to claim 18, wherein the rigid distal portion has a length equal to or less than 10 mm.

20. An electrosurgical forceps according to claim 18, wherein the sleeve comprising an encapsulated braid, wherein a density of the braid within the encapsulation is greater in the rigid distal portion than in the flexible proximal portion.

21. An electrosurgical forceps according to claim 1, wherein the pair of jaws are dimensioned to fit within an instrument channel of a surgical scoping device.

22. An electrosurgical apparatus comprising:
an electrosurgical generator for supplying microwave energy;
a surgical scoping device having an instrument cord for insertion into a patient's body, the instrument cord having an instrument channel extending therethrough;
an electrosurgical forceps according to claim 1 mounted in the instrument channel; and
a handle for actuating the forceps,
wherein the coaxial cable is connected at its proximal end to receive microwave energy from the electrosurgical generator, and
wherein the actuating element is operably connected to the handle.

23. An electrosurgical apparatus according to claim 22, wherein the actuating element is a sleeve that extends around and is axially slidably relative to the coaxial cable.

24. An electrosurgical apparatus according to claim 23, wherein the handle comprises an actuation mechanism for controlling axial movement of the sleeve, the actuation mechanism comprising:
a body fixed in the handle;
a carriage slidable relative to the body, and
a lever pivotably mounted on the body and operably engaged with the carriage, whereby rotation of the lever caused sliding motion of the carriage,
wherein the sleeve is attached to the carriage.

25. An electrosurgical apparatus according to claim 24, wherein the actuation mechanism includes a biasing element arranged to urge the carriage in a proximal direction.

* * * * *